(12) United States Patent
Washington (10) Patent No.: US 12,274,364 B2
(45) Date of Patent: Apr. 15, 2025

(54) BED WITH FLOWING WATER SOUND EFFECT

(71) Applicant: Travis Washington, Stockbridge, GA (US)

(72) Inventor: Travis Washington, Stockbridge, GA (US)

( * ) Notice: Subject to any disclaimer, the term of this patent is extended or adjusted under 35 U.S.C. 154(b) by 399 days.

(21) Appl. No.: 17/978,314

(22) Filed: Nov. 1, 2022

(65) Prior Publication Data
US 2024/0138578 A1   May 2, 2024

(51) Int. Cl.
*A47C 21/00* (2006.01)
*A47C 19/02* (2006.01)
*A47C 19/22* (2006.01)
*A61M 21/00* (2006.01)

(52) U.S. Cl.
CPC .......... *A47C 21/003* (2013.01); *A47C 19/022* (2013.01); *A47C 19/22* (2013.01); *A61M 2021/0027* (2013.01)

(58) Field of Classification Search
CPC ..... A47C 21/003; A47C 19/022; A47C 19/22; A61M 2021/0027; A61M 2021/0044; A61M 2205/3592; A61M 2205/505; A61M 2205/587; A61M 21/02
See application file for complete search history.

(56) References Cited

U.S. PATENT DOCUMENTS

| | | | | |
|---|---|---|---|---|
| 4,352,149 A | * | 9/1982 | Stetler | B44F 9/00 239/18 |
| 5,146,633 A | * | 9/1992 | Kim | A47C 21/048 5/284 |
| 5,234,728 A | * | 8/1993 | Chiang | B44F 1/00 40/406 |
| D398,422 S | | 9/1998 | Rooks | |
| 6,256,811 B1 | * | 7/2001 | Nelson | G09F 19/12 362/801 |
| 6,984,057 B1 | * | 1/2006 | Rogers | A47C 21/003 362/253 |
| 7,861,942 B2 | * | 1/2011 | Damon | B05B 17/085 239/18 |
| 7,922,103 B2 | | 4/2011 | Houstoun | |

(Continued)

FOREIGN PATENT DOCUMENTS

WO   2021007644   1/2021

*Primary Examiner* — Ziaul Karim
(74) *Attorney, Agent, or Firm* — Kyle A. Fletcher, Esq.

(57) ABSTRACT

The bed with flowing water sound effect maintains a flow of water. The turbulence generated by the flow of water generates a noise commonly called white noise. The bed with flowing water sound effect is positioned near a bed. The white noise generated by the bed with flowing water sound effect helps the patient to sleep. The bed with flowing water sound effect incorporates a fluid management structure, a control circuit, and the bed. The bed further comprises a headboard. The fluid management structure mounts and the control circuit mount in the headboard. The fluid management provides the flow paths and the motive forces necessary to generate the flow of water. The control circuit: a) controls the operation of the fluid management structure; b) provides the fluid management structure with electric energy; and, c) generates an illumination that is visible from the headboard.

15 Claims, 5 Drawing Sheets

(56) References Cited

U.S. PATENT DOCUMENTS

| | | | |
|---|---|---|---|
| 2005/0258268 A1* | 11/2005 | Watson | F21V 33/00 |
| | | | 239/23 |
| 2007/0125872 A1* | 6/2007 | Damon | B05B 17/085 |
| | | | 239/18 |
| 2008/0217424 A1 | 9/2008 | Yang | |
| 2011/0099905 A1 | 5/2011 | Rake | |
| 2020/0324309 A1 | 8/2020 | Lefebvre | |
| 2021/0204708 A1* | 7/2021 | Ludlum | G06F 3/167 |
| 2021/0386964 A1* | 12/2021 | Youngblood | A47C 27/085 |
| 2022/0023907 A1 | 1/2022 | Zimmerman | |

* cited by examiner

BED WITH FLOWING WATER SOUND EFFECT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of illuminated displays with flowing liquids. (G09F13/24)

SUMMARY OF INVENTION

The bed with flowing water sound effect is a therapeutic device. The bed with flowing water sound effect is adapted for use with a patient. The bed with flowing water sound effect maintains a flow of water. The turbulence generated by the flow of water generates a noise commonly called white noise. The bed with flowing water sound effect is positioned near a bed. The white noise generated by the bed with flowing water sound effect helps the patient to sleep. The bed with flowing water sound effect comprises a fluid management structure, a control circuit, and the bed. The bed further comprises a headboard. The fluid management structure mounts and the control circuit mount in the headboard. The fluid management provides the flow paths and the motive forces necessary to generate the flow of water. The control circuit: a) controls the operation of the fluid management structure; b) provides the fluid management structure with electric energy; and, c) generates an illumination that is visible from the headboard.

These together with additional objects, features and advantages of the bed with flowing water sound effect will be readily apparent to those of ordinary skill in the art upon reading the following detailed description of the presently preferred, but nonetheless illustrative, embodiments when taken in conjunction with the accompanying drawings.

In this respect, before explaining the current embodiments of the bed with flowing water sound effect in detail, it is to be understood that the bed with flowing water sound effect is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the bed with flowing water sound effect.

It is therefore important that the claims be regarded as including such equivalent construction insofar as they do not depart from the spirit and scope of the bed with flowing water sound effect. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
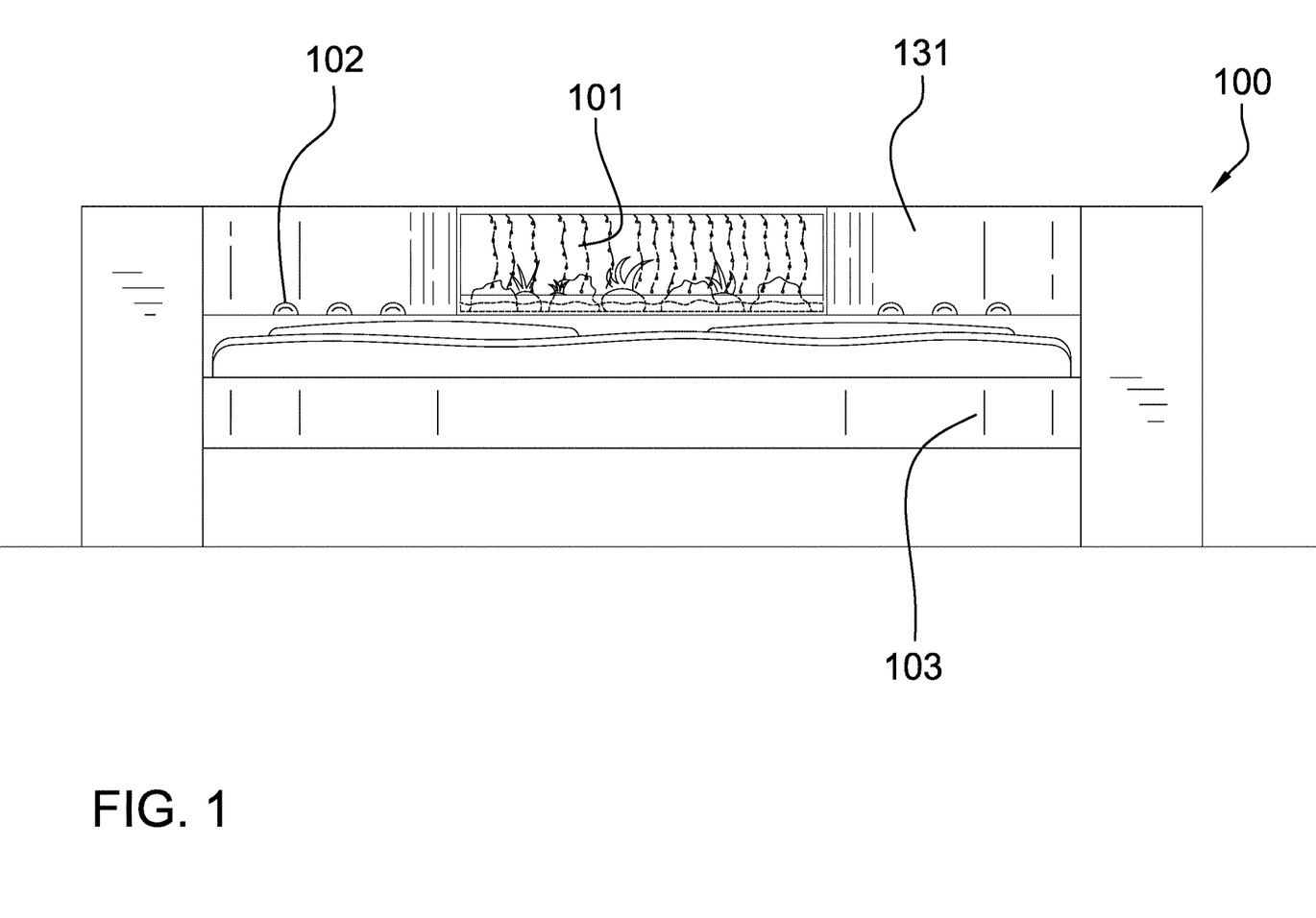
FIG. 1 is a front view of an embodiment of the disclosure.
Figure 2:
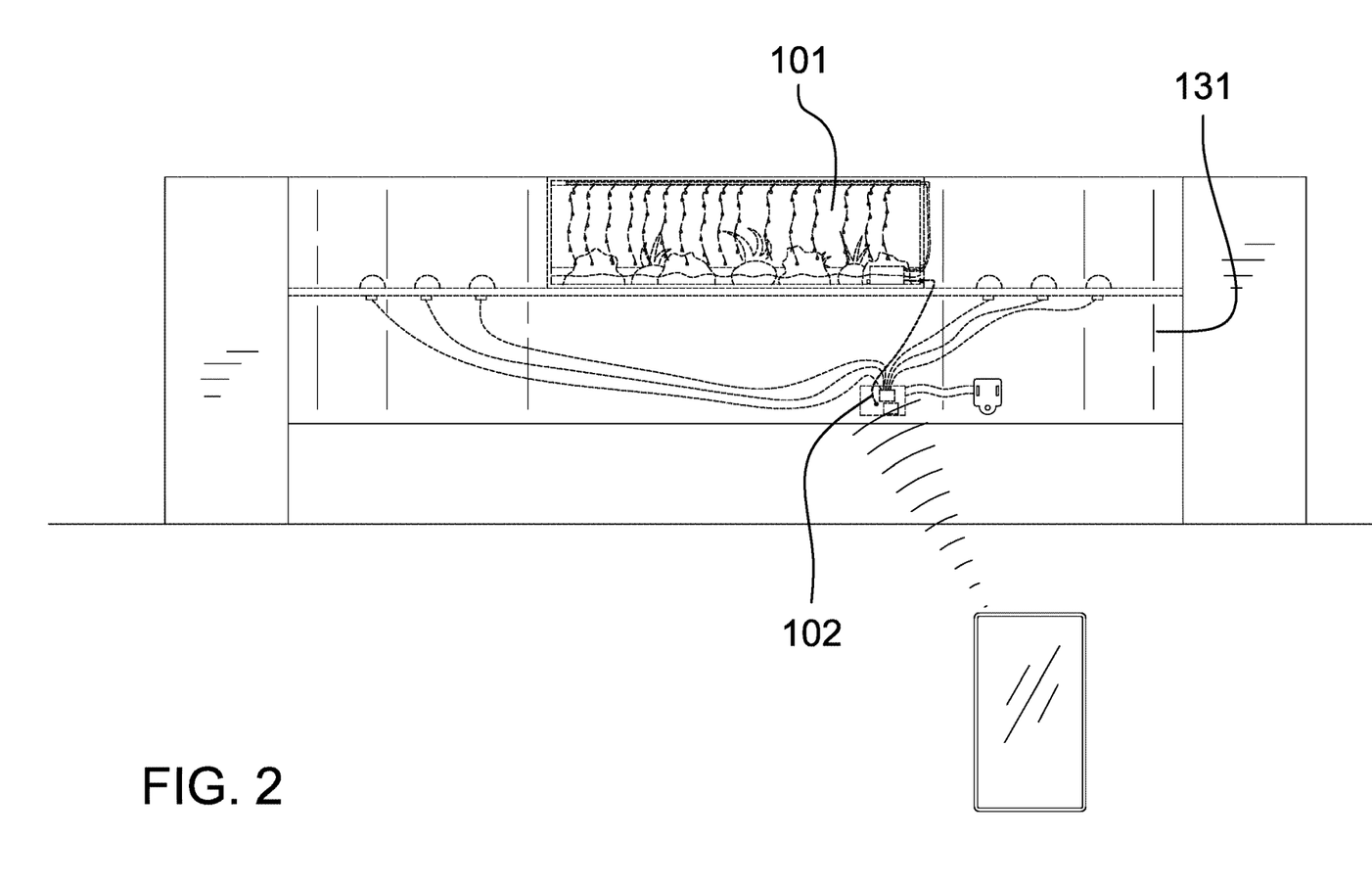
FIG. 2 is a side view of an embodiment of the disclosure.
Figure 3:
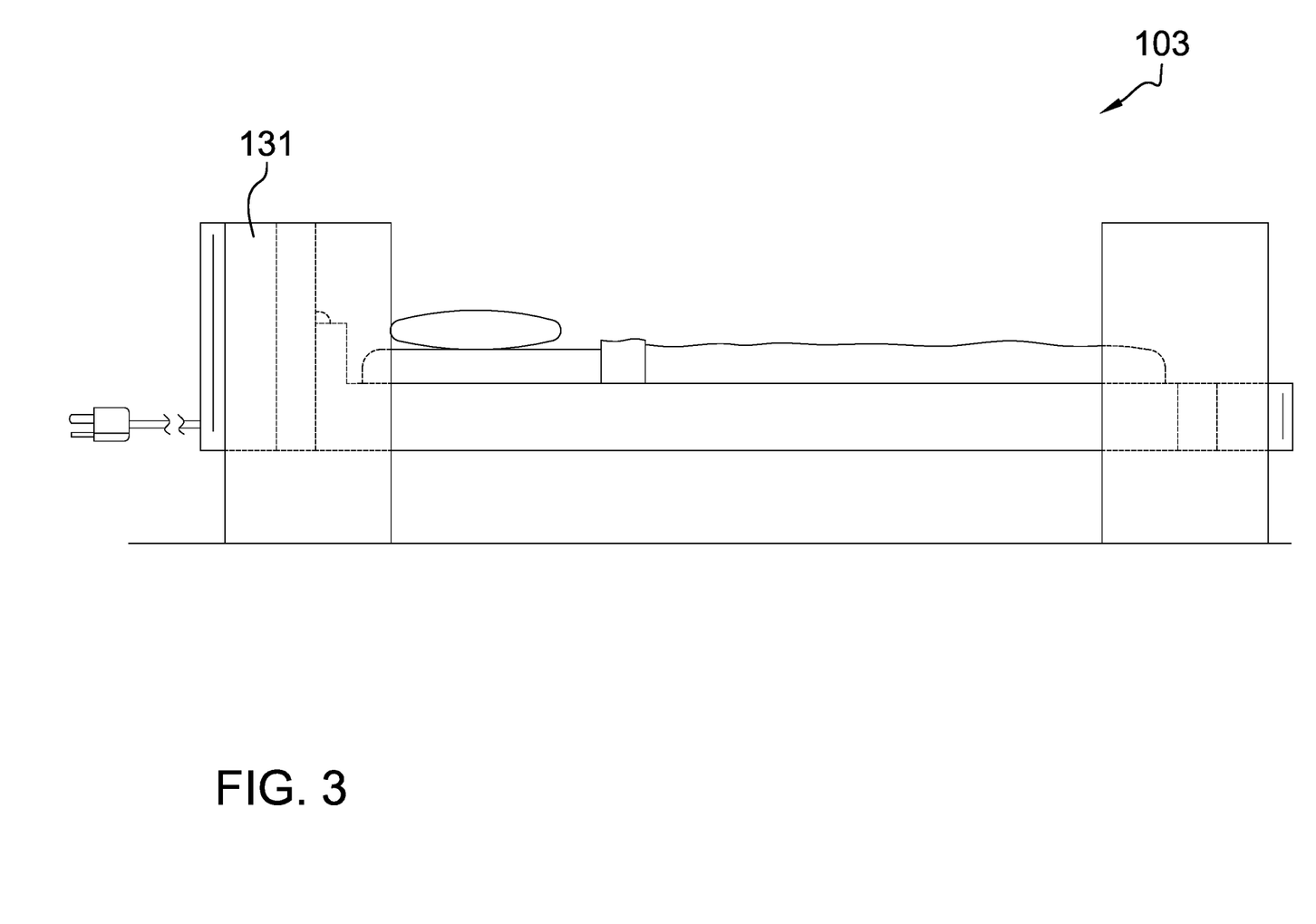
FIG. 3 is a rear view of an embodiment of the disclosure.
Figure 4:
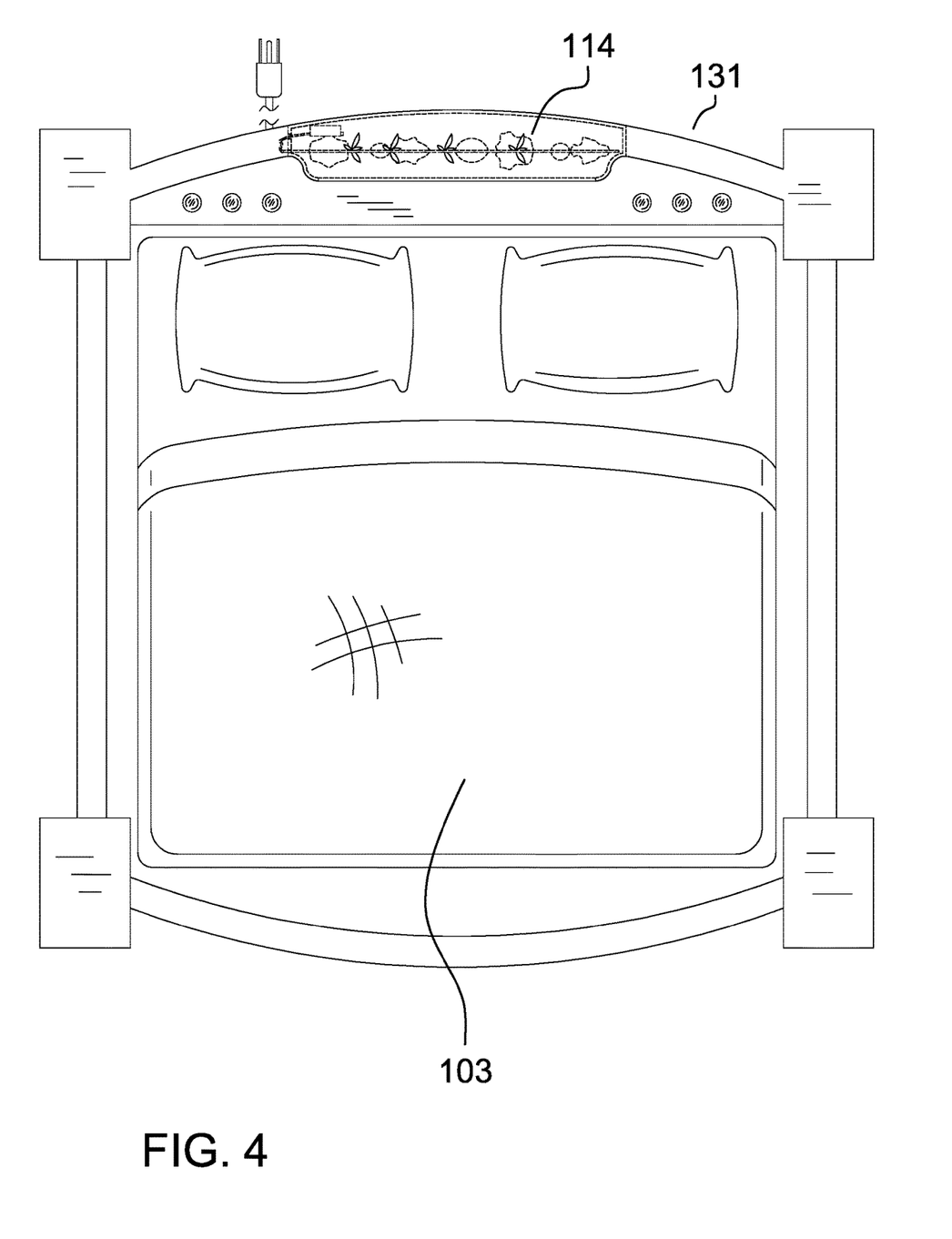
FIG. 4 is a top view of an embodiment of the disclosure.
Figure 5:
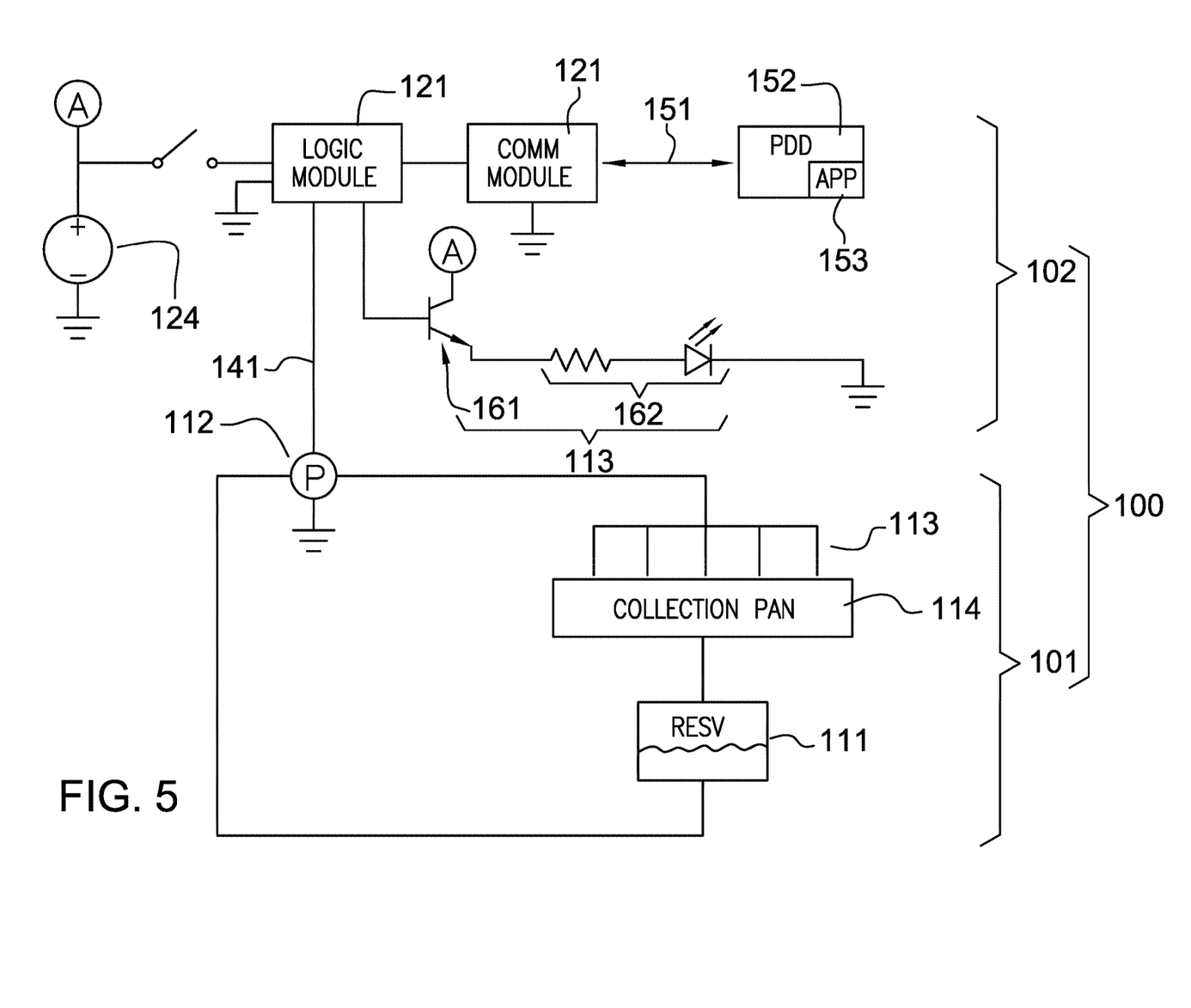
FIG. 5 is a schematic view of an embodiment of the disclosure.

Detailed reference will now be made to one or more potential embodiments of the disclosure, which are illustrated in FIGS. 1 through 5.

The bed with flowing water sound effect 100 (hereinafter invention) is a therapeutic device. The invention 100 is adapted for use with a patient. The invention 100 maintains a flow of water. The turbulence generated by the flow of water generates a noise commonly called white noise. The invention 100 is positioned near a bed 103. The white noise generated by the invention 100 helps the patient to sleep. The invention 100 comprises a fluid management structure 101, a control circuit 102, and the bed 103. The bed 103 further comprises a headboard 131. The fluid management structure 101 mounts and the control circuit 102 mount in the headboard 131. The fluid management provides the flow paths and the motive forces necessary to generate the flow of water. The control circuit 102: a) controls the operation of the fluid management structure 101; b) provides the fluid management structure 101 with electric energy; and, c) generates an illumination that is visible from the headboard 131.

The bed 103 is a furniture item. The bed 103 is defined elsewhere in this disclosure. The headboard 131 is a furniture item. The headboard 131 is defined elsewhere in this disclosure.

The fluid management structure 101 is a mechanical structure. The fluid management structure 101 manages the flow of water through the invention 100. The fluid management structure 101 stores the water that flows through the invention 100. The fluid management structure 101 generates the motive forces to pump the water through the invention 100. The fluid management structure 101 forms the fluid flow pathways used to transport water through the invention 100. The fluid management structure 101 forms an electric connection to the control circuit 102. The fluid management structure 101 draws electric energy from the control circuit 102. The fluid management structure 101 converts the received energy into the motive forces used to pump water through the invention 100.

The fluid management structure 101 comprises a reservoir structure 111, a circulation pump 112, a manifold 113, and a collection pan 114. The reservoir structure 111, the circulation pump 112, the manifold 113, and the collection pan 114 are fluidically interconnected to form a fluidic circuit.

The reservoir structure 111 is a fluid containment structure. The reservoir structure 111 forms a reservoir that stores the water flowing through the fluid management structure 101. The reservoir structure 111 is sized to contain all the water contained within the fluid management structure 101. The reservoir structure 111 forms a fluidic connection with the circulation pump 112. The reservoir structure 111 forms a fluidic connection with the collection pan 114. The circulation pump 112 draws water out of the reservoir structure 111. The reservoir structure 111 receives water from the collection pan 114. The water received from the collection pan 114 is gravity fed into the circulation pump 112.

The circulation pump 112 is a pump. The pump is defined elsewhere in this disclosure. The circulation pump 112 is an electrically powered device. The circulation pump 112 forms a fluidic connection with the reservoir structure 111. The circulation pump 112 forms a fluidic connection with the manifold 113. The circulation pump 112 converts electric energy received from the control circuit 102 into the motive forces that transport the water through the fluid management structure 101. The circulation pump 112 generates a pressure differential draws water from the reservoir structure 111. The pressure differential generated by the circulation pump 112 pumps water into the manifold 113. The pressure differential generated by the circulation pump 112 is adequate to discharge the water flowing through the manifold 113 into the collection pan 114.

The manifold 113 is a fluid network. The manifold 113 receives water from the circulation pump 112. The manifold 113 distributes the received water into a plurality of tubular structures. The manifold 113 discharges the received water from the plurality of tubular structures such that the discharged water is gravity fed into the collection pan 114. The water discharged from the manifold 113 generates an acoustic turbulence that can be heard as gravity draws the discharged water to the collection pan 114.

The collection pan 114 is a pan shaped structure. The collection pan 114 receives the water that is discharged from the manifold 113. The collection pan 114 accumulates the water that is discharged from the manifold 113. The collection pan 114 forms a fluidic connection with the reservoir structure 111 to complete the fluidic circuit of the invention 100. The collection pan 114 gravity feeds the received water back to the reservoir structure 111.

The control circuit 102 is an electric circuit. The control circuit 102 provides the electric energy needed to power the operation of the fluid management structure 101. The control circuit 102 controls the operation of the fluid management structure 101. By controlling the operation of the fluid management structure 101 is meant that the control circuit 102 initiates the operation of the fluid management structure 101 by allowing the flow of electric energy into the fluid management structure 101. By controlling the operation of the fluid management structure 101 is further meant that the control circuit 102 discontinues the operation of the fluid management structure 101 by discontinuing the flow of electric energy into the fluid management structure 101.

The control circuit 102 generates an illumination that is visible from the environment surrounding the headboard 131 of the bed 103. The control circuit 102 controls the illumination generated by the control circuit 102. By controlling the generated illumination of the control circuit 102 is meant that the control circuit 102 initiates the illumination of the environment surrounding the headboard 131. By controlling the generated illumination of the control circuit 102 is further meant that the control circuit 102 extinguishes the illuminated generated from the control circuit 102. By controlling the generated illumination of the control circuit 102 is finally meant that the control circuit 102 controls the amount of illumination generated by the control circuit 102.

The control circuit 102 comprises a logic module 121, a communication module 122, a lamp circuit 123, and a power circuit 124. The logic module 121, the communication module 122, the lamp circuit 123, and the power circuit 124 are electrically interconnected.

The logic module 121 is a readily and commercially available programmable electronic device that is used to manage, regulate, and operate the control circuit 102. The communication module 122 is a wireless electronic communication device that allows the logic module 121 to wirelessly communicate with a personal data device 152. The communication module 122 further comprises a wireless communication link 151 and the personal data device 152. The communication module 122 forms the wireless communication link 151 with the personal data device 152. The communication module 122 exchanges one or more direct messaging facilities that are transmitted over the wireless communication link 151 to the personal data device 152. The message contained in the direct messaging facility contains operating instructions for the logic module 121. The logic module 121 uses the received messaging facility to adjust the operation of the invention 100.

The personal data device 152 is a programmable electrical device. The personal data device 152 further comprises an application 153. The personal data device 152 provides data management and communication services through one or more functions referred to as an application 153. The application 153 is a set of logical operating instructions that are performed by the personal data device 152. The addition of an application 153 will provide increased functionality for the personal data device 152. This disclosure assumes that an application 153 exists for the purpose of interacting with the invention 100. Methods to design and implement an application 153 on a personal data device 152 are well known and documented in the electrical arts. The application 153 of the personal data device 152 forms an interface with the control circuit 102. The personal data device 152 transmits the messaging facility over the wireless communication link 151 to the control circuit 102. The communication module 122 receives the transmitted operating instructions and relays the received operating instructions to the logic module 121.

The logic module 121 controls the operation of the fluid management structure 101. By controlling the operation of the logic module 121 is meant that the logic module 121 initiates the operation of the fluid management structure 101 by allowing the flow of electric energy into the fluid management structure 101. By controlling the operation of the logic module 121 is further meant that the logic module 121 discontinues the operation of the fluid management structure 101 by discontinuing the flow of electric energy into the fluid management structure 101.

The logic module 121 generates an illumination that is visible from the environment surrounding the headboard 131 of the bed 103. The logic module 121 controls the illumination generated by the lamp circuit 123. By controlling the generated illumination of the lamp circuit 123 is meant that the logic module 121 initiates the illumination of the environment surrounding the headboard 131. By controlling the generated illumination of the lamp circuit 123 is further meant that the logic module 121 extinguishes the illuminated generated from the logic module 121. By controlling the generated illumination of the lamp circuit 123 is finally meant that the logic module 121 controls the amount of illumination generated by the logic module 121.

The logic module 121 further comprises a pump control signal 141. The pump control signal 141 is an electric signal that is transmitted from the logic module 121 to the circulation pump 112. The electric signal transmitted through pump control signal 141 signals the circulation pump 112 to initiate operation. The electric signal transmitted through pump control signal 141 further signals the circulation pump 112 to discontinue operation.

The lamp circuit 123 is an electric circuit. The lamp circuit 123 converts electric energy into illumination. The lamp circuit 123 generates the illumination that is visible from the environment surrounding the headboard 131. The lamp circuit 123 receives electric energy from the power circuit 124. The lamp circuit 123 electrically connects to the logic module 121. The logic module 121 controls the operation of the lamp circuit 123 by controlling the flow of electric energy from the power circuit 124 into the lamp circuit 123. The lamp circuit 123 further comprises an electrically controlled switch 161 and one or more illuminating elements 162.

The electrically controlled switch 161 is an electrical circuit element. The electrically controlled switch 161 is defined elsewhere in this disclosure. The electrically controlled switch 161 forms a switch that transfers electric energy from the power circuit 124 into the one or more illuminating elements 162. The electrically controlled switch 161 electrically connects to the logic module 121. The logic module 121 transmits a first electric signal that actuates the electrically controlled switch 161 to a closed position. The logic module 121 further transmits a second electric signal that actuates the electrically controlled switch 161 to an open position.

Each illuminating element selected from the one or more illuminating elements 162 converts electric energy into illumination. The one or more illuminating elements 162 draws electric energy from the power circuit 124 through the electrically controlled switch 161. The one or more illuminating elements 162 generates the illumination that is visible from the environment surrounding the headboard 131. In the first potential embodiment of the disclosure, the electrically controlled switch 161 is a transistor.

The power circuit 124 is an external power source. The power circuit 124 provides the electric energy needed to power the operation of both the control circuit 102 and the circulation pump 112.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Application or App: As used in this disclosure, an application or app is a self-contained piece of software that is especially designed or downloaded for use with a personal data device.

Barrier: As used in this disclosure, a barrier is a physical obstacle that forms a boundary between a first space and a second space. The barrier prevents the passage of an object between the first space and the second space.

Bed: As used in this disclosure, a bed refers to a structure, typically a furniture item, used for sleeping or resting. When the structure is a furniture item, the bed comprises a frame and a mattress. The frame is a pedestal that elevates the mattress. A bed often further comprises one or more box frames. The one or more box frames are mechanical structures that form secondary pedestals that elevate the mattress above the frame. A bed often further comprises a headboard. The headboard is a decorative element that forms a protective barrier between the bed and a wall the bed is placed next to.

Bluetooth™: As used in this disclosure, Bluetooth™ is a standardized communication protocol that is used to wirelessly interconnect electronic devices.

Cant: As used in this disclosure, a cant is an angular deviation from one or more reference lines (or planes) such as a vertical line (or plane) or a horizontal line (or plane).

Cavitation: As used in this disclosure, cavitation refers to a turbulence in a fluid flow wherein the energy of the turbulence causes a phase change within the fluid that commonly appear as bubbles.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Channel: As used in this disclosure, a channel is a previously determined frequency of electromagnetic radiation that is used for wireless communication. Wireless communication structures often designate a plurality of channels which allows users to "change the channel" when a previously specified channel is experiencing some form of interference.

Communication Link: As used in this disclosure, a communication link refers to the structured exchange of data between two objects.

Composite Prism: As used in this disclosure, a composite prism refers to a structure that is formed from a plurality of structures selected from the group consisting of a prism structure and a pyramid structure. The plurality of selected structures may or may not be truncated. The plurality of prism structures are joined together such that the center axes of each of the plurality of structures are aligned. The congruent ends of any two structures selected from the group consisting of a prism structure and a pyramid structure need not be geometrically similar.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Electrically Controlled Switch: As used in this disclosure, an electrically controlled switch refers to a switch used to control the flow of electricity through an electric circuit. The actuation of the electrically controlled switch is controlled by an electrical signal. Examples of electrically controlled switches include, but are not limited to, transistors and relays.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Exterior: As used in this disclosure, the exterior is used as a relational term that implies that an object is not contained within the boundary of a structure or a space.

Extinguish: As used in this disclosure, to extinguish means to cause a device to stop generating an illumination.

Environment: As used in this disclosure, an environment refers to the physical conditions surrounding an object. The term environment is often limited to the physical conditions that the object interacts with.

External Power Source: As used in this disclosure, an external power source is a source of the energy that is externally provided to enable the operation of the present disclosure. Examples of external power sources include, but are not limited to, electrical power sources and compressed air sources.

Flow: As used in this disclosure, a flow refers to the passage of a fluid past a fixed point. This definition considers bulk solid materials as capable of flow.

Fluid: As used in this disclosure, a fluid refers to a state of matter wherein the matter is capable of flow and takes the shape of a container it is placed within. The term fluid commonly refers to a liquid or a gas.

Fluid Impermeable: As used in this disclosure, the term fluid impermeable refers to: a) the ability of a structure to not allow a fluid to pass through the structure; or, b) the ability of a material not absorb through the exterior surfaces of the material a fluid that the material is immersed in or exposed to.

Fluidic Circuit: As used in this disclosure, a fluidic circuit is a closed loop path through which a fluid flows. The closed loop will generally initiate and terminate at reservoir.

Fluidic Connection: As used in this disclosure, a fluidic connection refers to a tubular structure that transports a fluid from a first object to a second object. Methods to design and use fluidic connections are well-known and documented in the mechanical, chemical, and plumbing arts.

Fluid Network: As used in this disclosure, a fluid network refers to a transport structure that: a) receives a fluid into the fluid network; b) transports the fluid through a series of pipes, valves, and manifolds; and, c) discharges the fluid from the fluid network.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Gas: As used in this disclosure, a gas refers to a state (phase) of matter that is fluid and that fills the volume of the structure that contains it. Stated differently, the volume of a gas always equals the volume of its container.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Illumination: As used in this disclosure, illumination refers to electromagnetic radiation contained with an area. Illumination is a synonym for light, particularly in cases where a measure of the amount of visible electromagnetic radiation in a space is called for. The verb form of illumination is to illuminate and is taken to mean the generation of an illumination.

Inferior: As used in this disclosure, the term inferior refers to a directional reference that is parallel to and in the same direction as the force of gravity when an object is positioned or used normally.

Interior: As used in this disclosure, the interior is used as a relational term that implies that an object is contained within the boundary of a structure or a space.

Lamp: As used in this disclosure, a lamp is an electrical device that generates visible light to illuminate objects so they can be seen.

Light: As used in this disclosure, light refers to electromagnetic radiation that illuminates an area.

Illumination is a synonym for light, particularly in cases where a measure of the amount of light in a space is called for.

Liquid: As used in this disclosure, a liquid refers to a state (phase) of matter that is fluid and that maintains, for a given pressure, a fixed volume that is independent of the volume of the container.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Logic Module: As used in this disclosure, a logic module is a readily and commercially available electrical device that accepts digital and analog inputs, processes the digital and analog inputs according to previously specified logical processes and provides the results of these previously specified logical processes as digital or analog outputs. The disclosure allows, but does not assume, that the logic module is programmable.

Maintained Switch: As used in this disclosure, a maintained switch is a switch that maintains the position that was set in the most recent switch actuation. A maintained switch works in an opposite manner to a momentary switch.

Manifold: As used in this disclosure, a manifold is a pipe or chamber having several ports through which one or more fluids are gathered or distributed.

Messaging Facility: As used in this disclosure, a messaging facility is a previously determined formatting structure through which a text or image (referred to in this definition as text) based communication is transmitted for delivery. A messaging facility is selected from the group consisting of a traditional messaging facility, a direct messaging facility and a broadcast messaging facility. A traditional messaging facility includes the delivery of a physical object containing the text based communication. The direct messaging facility includes communications that are addressed to a previously identified group of recipients. The broadcast messaging facility includes communications that are transmitted without the prior identification of the intended group of recipients. An example of a traditional messaging facility includes, but is not limited to, postal delivery. Examples of a direct messaging facilities include, but are not limited to, email, audio based communications, and SMS messages. A social media service is an example of a broadcast messaging facility.

Momentary Switch: As used in this disclosure, a momentary switch is a biased switch in the sense that the momentary switch has a baseline position that only changes when the momentary switch is actuated (for example when a pushbutton switch is pushed or a relay coil is energized). The momentary switch then returns to the baseline position once the actuation is completed. This baseline position is called the "normal" position. For example, a "normally open" momentary switch interrupts (open) the electric circuit in the baseline position and completes (closes) the circuit when the momentary switch is activated. Similarly, a "normally closed" momentary switch will complete (close) an electric circuit in the baseline position and interrupt (open) the circuit when the momentary switch is activated.

Negative Space: As used in this disclosure, negative space is a method of defining an object through the use of open or empty space as the definition of the object itself, or, through the use of open or empty space to describe the boundaries of an object.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Pan: As used in this disclosure, a pan is a hollow and prism-shaped containment structure. The pan has a single open face. The open face of the pan is often, but not always, the superior face of the pan. The open face is a surface selected from the group consisting of: a) a congruent end of the prism structure that forms the pan; and, b) a lateral face of the prism structure that forms the pan. A semi-enclosed pan refers to a pan wherein the closed end of prism structure of the pan and/or a portion of the closed lateral faces of the pan are open.

Patient: As used in this disclosure, a patient is a person who is designated to receive a medical treatment, therapy, or service. The term patient may be extended to an animal when used within the context of the animal receiving veterinary treatment or services.

PDD: As used in this disclosure, PDD is an acronym for personal data device.

Perimeter: As used in this disclosure, a perimeter is one or more curved or straight lines that bounds an enclosed area on a plane or surface. The perimeter of a circle is commonly referred to as a circumference.

Personal Data Device: As used in this disclosure, a personal data device is a handheld logical device that is used for managing personal information and communication. Examples of personal data device include, but are not limited to, cellular phones, tablets, and smartphones.

Perimetrical Boundary: As used in this disclosure, a perimetrical boundary is a hypothetical rectangular block that contains an object. Specifically, the rectangular block selected to be the perimetrical boundary is the rectangular block with the minimum volume that fully contains the object. In a two-dimensional structure, the perimetrical boundary is the rectangle with the minimum surface area.

Phase: As used in this disclosure, phase refers to the state of the form of matter. The common states of matter are solid, liquid, gas, and plasma.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Protected Space: As used in this disclosure, a protected space is a negative space within which an object is stored.

The protected space is enclosed by a barrier structure that: a) prevents damage to the object contained within the protected space; b) maintains conditions that are appropriate for the object; c) protects the object within the protected space from potential dangers that are outside of the protected space; or, d) maintains the privacy of the object within the protected space.

Pump: As used in this disclosure, a pump is a mechanical device that uses suction or pressure to raise or move fluids, compress fluids, or force a fluid into an inflatable object. Within this disclosure, a compressor refers to a pump that is dedicated to compressing a fluid or placing a fluid under pressure.

Remote Control: As used in this disclosure, remote control means the establishment of control of a device from a distance. Remote control is generally accomplished through the use of an electrical device that generates electrically based control signals that are transmitted via radio frequencies or other means to the device.

Solid: As used in this disclosure, a solid refers to a state (phase) of matter that: 1) has a fixed volume; and, 2) does not flow.

Superior: As used in this disclosure, the term superior refers to a directional reference that is parallel to and in the opposite direction of the force of gravity when an object is positioned or used normally.

Supporting Surface: As used in this disclosure, a supporting surface is a horizontal surface upon which an object is placed and to which the load of the object is transferred. This disclosure assumes that an object placed on the supporting surface is in an orientation that is appropriate for the normal or anticipated use of the object.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Therapeutic: As used in this disclosure, therapeutic is an adjective that refers to a medical, ameliorative, or hygienic substance, process, procedure, or device.

Transistor: As used in this disclosure, a transistor is a general term for a three terminal semiconducting electrical device that is used for electrical signal amplification and electrical switching applications. There are several designs of transistors. A common example of a transistor is an NPN transistor that further comprises a collector terminal, an emitter terminal, and a base terminal and which consists of a combination of two rectifying junctions (a diode is an example of a rectifying junction). Current flowing from the collector terminal through the emitter terminal crosses the two rectifier junctions. The amount of the electric current crossing the two rectified junctions is controlled by the amount of electric current that flows through the base terminal. This disclosure assumes the use of an NPN transistor. This assumption is made solely for the purposes of simplicity and clarity of exposition. Those skilled in the electrical arts will recognize that other types of transistors, including but not limited to, field effect transistors and PNP transistors, can be substituted for an NPN transistor without undue experimentation. The transistors used in this disclosure operate in either an amplifier mode or a switch mode. In the amplifier mode, when a first current flows into the base, a second current flows from the collector to the emitter. The amount of the second current is a linear function of the first current. In this mode, the transistor acts as an amplifier. The operation of a transistor moves to a switching mode when the first current reaches the saturation levels of the transistor. In the switch mode, when a voltage is applied to the base, current will flow into the base and the transistor will act like a closed switch allowing current to flow from the collector to the emitter. When the voltage is removed from the base, the transistor will act like an open switch disrupting current flow from the collector to the emitter.

Tube: As used in this disclosure, the term tube is used to describe a hollow prism-shaped device with two congruent open ends. While tubes that are suitable for use in this disclosure are often used to transport or conveys fluids or gases, the purpose of the tubes in this disclosure are structural. In this disclosure, the terms inner dimension and outer dimension of a tube are used as they would be used by those skilled in the plumbing arts.

Turbulence: As used in this disclosure, turbulence describes the motion or flow of a fluid wherein the velocities and pressures within the fluid flow will vary randomly or in an incalculably complex fashion.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

WiFi™: As used in this disclosure, WiFi™ refers to the physical implementation of a collection of wireless electronic communication standards commonly referred to as IEEE 802.11x.

Wireless: As used in this disclosure, wireless is an adjective that is used to describe a communication link between two devices that does not require the use of physical cabling.

Wireless Communication Link: As used in this disclosure, a wireless communication link is a previously determined channel that is used to wirelessly exchange information between one or more transceivers.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A bed with flowing water sound effect comprising a fluid management structure, a control circuit, and the bed;
   wherein the bed further comprises a headboard;
   wherein the fluid management structure mounts and the control circuit mount in the headboard;

wherein the bed with flowing water sound effect is a therapeutic device;

wherein the bed with flowing water sound effect is adapted for use with a patient;

wherein the bed with flowing water sound effect maintains a flow of water;

wherein the flow of water generates a noise called white noise;

wherein the bed with flowing water sound effect is positioned near the bed;

wherein the fluid management provides the flow paths and the motive forces necessary to generate the flow of water;

wherein the control circuit: a) controls the operation of the fluid management structure; b) provides the fluid management structure with electric energy; and, c) generates an illumination that is visible from the headboard.

2. The bed with flowing water sound effect according to claim 1, wherein the bed is a furniture item;

wherein the headboard is a furniture item.

3. The bed with flowing water sound effect according to claim 2, wherein the fluid management structure is a mechanical structure;

wherein the fluid management structure manages the flow of water through the bed with flowing water sound effect;

wherein the fluid management structure stores the water that flows through the bed with flowing water sound effect;

wherein the fluid management structure forms an electric connection to the control circuit;

wherein the fluid management structure draws electric energy from the control circuit;

wherein the fluid management structure converts the received energy into the motive forces used to pump water through the bed with flowing water sound effect.

4. The bed with flowing water sound effect according to claim 3, wherein the control circuit is an electric circuit;

wherein the control circuit provides the electric energy needed to power the operation of the fluid management structure;

wherein the control circuit controls the operation of the fluid management structure;

wherein by controlling the operation of the fluid management structure is meant that the control circuit initiates the operation of the fluid management structure by allowing the flow of electric energy into the fluid management structure;

wherein by controlling the operation of the fluid management structure is further meant that the control circuit discontinues the operation of the fluid management structure by discontinuing the flow of electric energy into the fluid management structure;

wherein the control circuit generates an illumination that is visible from the environment surrounding the headboard of the bed;

wherein the control circuit controls the illumination generated by the control circuit;

wherein by controlling the generated illumination of the control circuit is meant that the control circuit initiates the illumination of the environment surrounding the headboard;

wherein by controlling the generated illumination of the control circuit is further meant that the control circuit extinguishes the illuminated generated from the control circuit;

wherein by controlling the generated illumination of the control circuit is finally meant that the control circuit controls the amount of illumination generated by the control circuit.

5. The bed with flowing water sound effect according to claim 4, wherein the fluid management structure comprises a reservoir structure, a circulation pump, a manifold, and a collection pan;

wherein the reservoir structure, the circulation pump, the manifold, and the collection pan are fluidically interconnected to form a fluidic circuit.

6. The bed with flowing water sound effect according to claim 5, wherein the control circuit comprises a logic module, a communication module, a lamp circuit, and a power circuit;

wherein the logic module, the communication module, the lamp circuit, and the power circuit are electrically interconnected.

7. The bed with flowing water sound effect according to claim 6, wherein the reservoir structure is a fluid containment structure;

wherein the reservoir structure forms a reservoir that stores the water flowing through the fluid management structure;

wherein the reservoir structure is sized to contain all the water contained within the fluid management structure;

wherein the reservoir structure forms a fluidic connection with the circulation pump;

wherein the reservoir structure forms a fluidic connection with the collection pan;

wherein the circulation pump draws water out of the reservoir structure;

wherein the reservoir structure receives water from the collection pan.

8. The bed with flowing water sound effect according to claim 7, wherein the circulation pump is a pump;

wherein the circulation pump is an electrically powered device;

wherein the circulation pump forms a fluidic connection with the reservoir structure;

wherein the circulation pump forms a fluidic connection with the manifold;

wherein the circulation pump converts electric energy received from the control circuit into the motive forces that transport the water through the fluid management structure;

wherein the circulation pump generates a pressure differential draws water from the reservoir structure;

wherein the pressure differential generated by the circulation pump pumps water into the manifold;

wherein the pressure differential generated by the circulation pump is adequate to discharge the water flowing through the manifold into the collection pan.

9. The bed with flowing water sound effect according to claim 8, wherein the manifold is a fluid network;

wherein the manifold receives water from the circulation pump;

wherein the manifold distributes the received water into a plurality of tubular structures;

wherein the manifold discharges the received water from the plurality of tubular structures such that the discharged water is gravity fed into the collection pan.

10. The bed with flowing water sound effect according to claim 9, wherein the collection pan is a pan shaped structure;

wherein the collection pan receives the water that is discharged from the manifold;

wherein the collection pan accumulates the water that is discharged from the manifold;

wherein the collection pan forms a fluidic connection with the reservoir structure to complete the fluidic circuit of the bed with flowing water sound effect.

11. The bed with flowing water sound effect according to claim 10, wherein the logic module is a programmable electronic device;

wherein the communication module further comprises a wireless communication link and the personal data device;

wherein the communication module forms a wireless communication link with the personal data device;

wherein the communication module exchanges one or more direct messaging facilities that are transmitted over the wireless communication link to the personal data device;

wherein the message in the direct messaging facility contains operating instructions for the logic module;

wherein the logic module uses the received messaging facility to adjust the operation of the bed with flowing water sound effect.

12. The bed with flowing water sound effect according to claim 11, wherein the logic module controls the operation of the fluid management structure;

wherein by controlling the operation of the logic module is meant that the logic module initiates the operation of the fluid management structure by allowing the flow of electric energy into the fluid management structure;

wherein by controlling the operation of the logic module is further meant that the logic module discontinues the operation of the fluid management structure by discontinuing the flow of electric energy into the fluid management structure;

wherein the logic module generates an illumination that is visible from the environment surrounding the headboard of the bed;

wherein the logic module controls the illumination generated by the lamp circuit;

wherein by controlling the generated illumination of the lamp circuit is meant that the logic module initiates the illumination of the environment surrounding the headboard;

wherein by controlling the generated illumination of the lamp circuit is further meant that the logic module extinguishes the illuminated generated from the logic module;

wherein by controlling the generated illumination of the lamp circuit is finally meant that the logic module controls the amount of illumination generated by the logic module.

13. The bed with flowing water sound effect according to claim 12, wherein the logic module further comprises a pump control signal;

wherein the pump control signal is an electric signal that is transmitted from the logic module to the circulation pump;

wherein the electric signal transmitted through pump control signal signals the circulation pump to initiate operation;

wherein the electric signal transmitted through pump control signal further signals the circulation pump to discontinue operation.

14. The bed with flowing water sound effect according to claim 13, wherein the lamp circuit is an electric circuit;

wherein the lamp circuit converts electric energy into illumination;

wherein the lamp circuit generates the illumination that is visible from the environment surrounding the headboard;

wherein the lamp circuit receives electric energy from the power circuit;

wherein the lamp circuit electrically connects to the logic module;

wherein the logic module controls the operation of the lamp circuit by controlling the flow of electric energy from the power circuit into the lamp circuit.

15. The bed with flowing water sound effect according to claim 13, wherein the lamp circuit further comprises an electrically controlled switch and one or more illuminating elements;

wherein the electrically controlled switch is an electrical circuit element;

wherein the electrically controlled switch forms a switch that transfers electric energy from the power circuit into the one or more illuminating elements;

wherein the electrically controlled switch electrically connects to the logic module;

wherein the logic module transmits a first electric signal that actuates the electrically controlled switch to a closed position;

wherein the logic module further transmits a second electric signal that actuates the electrically controlled switch to an open position;

wherein each illuminating element selected from the one or more illuminating elements converts electric energy into illumination;

wherein the one or more illuminating elements draws electric energy from the power circuit through the electrically controlled switch;

wherein the one or more illuminating elements generates the illumination that is visible from the environment surrounding the headboard.

* * * * *